(12) United States Patent
Anderson et al.

(10) Patent No.: US 9,549,773 B2
(45) Date of Patent: *Jan. 24, 2017

(54) METHOD AND APPARATUS FOR DERMATOLOGICAL HYPOPIGMENTATION

(71) Applicant: The General Hospital Corporation, Boston, MA (US)

(72) Inventors: Richard Rox Anderson, Boston, MA (US); Dieter Manstein, Coral Gables, FL (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/004,439

(22) Filed: Jan. 22, 2016

(65) Prior Publication Data

US 2016/0157915 A1 Jun. 9, 2016

Related U.S. Application Data

(63) Continuation of application No. 13/057,939, filed as application No. PCT/US2009/053153 on Aug. 7, 2009.

(Continued)

(51) Int. Cl.
*A61B 18/02* (2006.01)
*A61F 7/00* (2006.01)
(Continued)

(52) U.S. Cl.
CPC .......... *A61B 18/0218* (2013.01); *A61F 7/00* (2013.01); *A61F 7/007* (2013.01); *A61F 7/0085* (2013.01);
(Continued)

(58) Field of Classification Search
CPC .......... A61B 2018/0047; A61F 7/0085; A61F 7/007; A61F 2007/0075; A61F 2007/0095
See application file for complete search history.

(56) References Cited

U.S. PATENT DOCUMENTS 3,664,344 A 5/1972 Bryne
4,206,609 A 6/1980 Durenec
(Continued)

FOREIGN PATENT DOCUMENTS

DE 9217897 11/1993
EP 1797847 6/2007
(Continued)

OTHER PUBLICATIONS

The Isreali Office Action Patent Application No. 211109 dated on Dec. 27, 2015.

(Continued)

*Primary Examiner* — Joseph Stoklosa
*Assistant Examiner* — Eunhwa Kim
(74) *Attorney, Agent, or Firm* — Andrews Kurth Kenyon LLP (57) ABSTRACT

Exemplary embodiments of the present disclosure provide method and apparatus for effecting (e.g., lightening) an appearance of skin by cooling or freezing small separated surface regions of the skin to produce regions of local hypopigmentation. The width of the regions can be, for example, smaller than about 1 mm or 0.5 mm, and a distance between these frozen regions can be greater than about 3 times the width of the regions. An exemplary apparatus can be provided that includes a plurality of spatially-separated thermally conductive arrangements that can be affixed or otherwise coupled to a base. For example, the conductive arrangements can be regions of conductive material provided in or proximal to a thermal insulator, or thermally (Continued)

conductive protrusions affixed to the base. The conductive arrangements can be cooled and then contacted with the skin surface to produce the small regions of hypopigmentation.

18 Claims, 6 Drawing Sheets

Related U.S. Application Data (60) Provisional application No. 61/087,036, filed on Aug. 7, 2008.

(51) Int. Cl.
| | | |
|---|---|---|
| *A61F 7/10* | (2006.01) | |
| *A61M 35/00* | (2006.01) | |
| *A61B 17/00* | (2006.01) | |
| *A61B 18/00* | (2006.01) | |
| *A61B 18/14* | (2006.01) | |
| *A61F 7/02* | (2006.01) | |

(52) U.S. Cl.
CPC ............ *A61F 7/10* (2013.01); *A61M 35/003* (2013.01); *A61B 2017/00747* (2013.01); *A61B 2018/00005* (2013.01); *A61B 2018/0047* (2013.01); *A61B 2018/00458* (2013.01); *A61B 2018/00577* (2013.01); *A61B 2018/00714* (2013.01); *A61B 2018/00815* (2013.01); *A61B 2018/00821* (2013.01); *A61B 2018/0237* (2013.01); *A61B 2018/0293* (2013.01); *A61B 2018/143* (2013.01); *A61F 2007/0052* (2013.01); *A61F 2007/0056* (2013.01); *A61F 2007/0063* (2013.01); *A61F 2007/0075* (2013.01); *A61F 2007/0086* (2013.01); *A61F 2007/0087* (2013.01); *A61F 2007/0089* (2013.01); *A61F 2007/0095* (2013.01); *A61F 2007/0096* (2013.01); *A61F 2007/0292* (2013.01)

(56) References Cited

U.S. PATENT DOCUMENTS

| | | | |
|---|---|---|---|
| 5,596,875 A | 1/1997 | Berry et al. | |
| 5,759,182 A | 6/1998 | Varney et al. | |
| 5,848,981 A | 12/1998 | Herbranson | |
| 5,901,707 A | 5/1999 | Goncalves | |
| 6,017,337 A * | 1/2000 | Pira ....................... | A61B 18/02 601/15 |
| 6,430,956 B1 | 8/2002 | Haas et al. | |
| 6,503,246 B1 | 1/2003 | Har-Shai et al. | |
| 6,629,417 B2 | 10/2003 | Haas et al. | |
| 6,981,970 B2 | 1/2006 | Karni | |
| 7,630,774 B2 | 12/2009 | Karni et al. | |
| 7,751,452 B2 | 7/2010 | Vogler | |
| 7,850,683 B2 | 12/2010 | Elkins | |
| 8,150,532 B2 | 4/2012 | Karni et al. | |
| 8,435,194 B2 | 5/2013 | Dverin et al. | |
| 8,579,835 B2 | 11/2013 | Britva et al. | |
| 8,950,406 B2 | 2/2015 | Karnj | |
| 2002/0120260 A1 | 8/2002 | Morris et al. | |
| 2003/0100936 A1 | 5/2003 | Altshuler et al. | |
| 2004/0167592 A1* | 8/2004 | Grove .................. | A61B 18/082 607/96 |
| 2004/0215294 A1* | 10/2004 | Littrup .................. | A61B 18/02 607/96 |
| 2005/0222565 A1 | 10/2005 | Manstein | |
| 2006/0058238 A1 | 3/2006 | Laurent-Applegate et al. | |
| 2006/0189976 A1 | 8/2006 | Karni et al. | |
| 2007/0088386 A1 | 4/2007 | Babaev | |
| 2007/0129714 A1 | 6/2007 | Elkins et al. | |
| 2007/0135876 A1 | 6/2007 | Weber | |
| 2007/0185527 A1 | 8/2007 | Babaev | |
| 2008/0039747 A1 | 2/2008 | Baerwalde et al. | |
| 2008/0119839 A1 | 5/2008 | Vancalette | |
| 2008/0183164 A1* | 7/2008 | Elkins .................... | A61B 18/02 606/21 |
| 2008/0183167 A1 | 7/2008 | Britva et al. | |
| 2008/0287943 A1 | 11/2008 | Weber et al. | |
| 2009/0012585 A1 | 1/2009 | Karni et al. | |
| 2009/0171424 A1 | 7/2009 | Britva et al. | |
| 2009/0254076 A1 | 10/2009 | Altshuler et al. | |
| 2009/0281537 A1 | 11/2009 | Britva et al. | |
| 2010/0036295 A1 | 2/2010 | Altshuler et al. | |
| 2010/0114007 A1 | 5/2010 | Fischer et al. | |
| 2012/0041525 A1 | 2/2012 | Karni et al. | |
| 2012/0071794 A1 | 3/2012 | Karni | |
| 2012/0123319 A1 | 5/2012 | Britva et al. | |
| 2012/0330194 A1 | 12/2012 | Britva et al. | |
| 2014/0007895 A1 | 1/2014 | Britva et al. | |
| 2014/0135662 A1 | 5/2014 | Britva et al. | |
| 2015/0045857 A1 | 2/2015 | Britva et al. | |
| 2015/0080991 A1 | 3/2015 | Britva et al. | |

FOREIGN PATENT DOCUMENTS

| | | |
|---|---|---|
| EP | 2201917 | 6/2010 |
| EP | 2272455 | 1/2011 |
| GB | 2286660 | 8/1995 |
| JP | 04-133822 | 12/1992 |
| JP | 10-052475 | 2/1998 |
| KR | 20-0431404 | 11/2006 |
| KR | 10-0802155 | 2/2008 |
| RU | 2074680 | 3/1997 |
| WO | WO 03/078596 | 9/2003 |
| WO | WO 2005/096979 | 10/2005 |
| WO | WO 2006/066226 | 6/2006 |
| WO | WO 2006/127467 | 11/2006 |
| WO | WO 2007/064718 | 6/2007 |
| WO | WO2008055243 | 5/2008 |
| WO | WO 2008/091983 | 7/2008 |
| WO | WO2008083305 | 7/2008 |
| WO | WO 2009/146053 | 12/2009 |
| WO | WO 2010/017477 | 2/2010 |
| WO | WO2013075006 | 5/2013 |
| WO | WO2013075016 | 5/2013 |

OTHER PUBLICATIONS

U.S. Appl. No. 60/886,587, filed Jan. 25, 2007, Bryan Weber.
U.S. Appl. No. 61/041,593, filed Apr. 1, 2008, Dieter Manstein.
U.S. Appl. No. 61/174,004, filed Apr. 30, 2009, Karni.
International Search Report for International Patent Application No. PCT/US2012/065664 mailed on Mar. 14, 2013.
International Written Opinion for International Patent Application No. PCT/US2012/065664 mailed on Mar. 14, 2013.
International Search Report for International Patent Application No. PCT/US2012/065643 mailed on Mar. 14, 2013.
International Written Opinion for International Patent Application No. PCT/US2012/065643 mailed on Mar. 14, 2013.
International Search Report and Written Opinion for International Application No. PCT/US2009/053153 mailed May 11, 2010.
Y. Har-shai et al. "Effect of Skin Temperature on Skin Pigmentation During Contact and Intralesional Cryosurgery of Keloids" JEADV 2007,21, pp. 191-198 (2006).
The Office Action for European Patent Application No. 09805610.4 dated on Feb. 10, 2015.
The Second Office Action for Chinese Patent Application No. 200980134959.1 mailed on Jul. 17, 2014.
Israeli Office Action for Israeli Patent Application No. 211109 mailed on Jun. 19, 2012.
European Search Report for European Application No. 09805610.4 mailed on Aug. 2, 2012.
Chinese Office Action for Chinese Patent Application No. 200980134959.1 mailed on Mar. 29, 2013.
Office Action for Korean Patent Application No. 10-2011-7005048 mailed on Oct. 21, 2015.

(56) References Cited

OTHER PUBLICATIONS

The Chinese Office Action mailed on Apr. 29, 2016 for Chinese Patent Application No. 201510026052.0.
The Korean Office Action dated on Jun. 23, 2016 for Korean Patent Application No. 10-2011-7005048.
The Isreali Office Action Patent Application No. 211109 mailed May 22, 2014.
The Japan Office Action Patent Application No. 2011-522276 dated on Aug. 29, 2013.
Yeh C. (1998) Cryosurgical Treatment of Melanin-Pigmented Gingiva. Oral Surg Oral Med or Pathol Oral Dariol Endod 86;660-3.
Thai K., and Sinclair R.D. (1999) Cryosurgery of Bening Skin Lesions. 40:175-186.

* cited by examiner

METHOD AND APPARATUS FOR DERMATOLOGICAL HYPOPIGMENTATION

CROSS REFERENCE TO RELATED APPLICATION

This application is a continuation of U.S. patent application Ser. No. 13/057,939 filed in Feb. 7, 2011, which claims priority from International Patent Application No. PCT/US2009/053153 filed Aug. 7, 2009, and from U.S. Provisional Patent Application Ser. No. 61/087,036 filed Aug. 7, 2008, the disclosures of which are incorporated herein by reference in their entireties.

TECHNICAL FIELD

The present disclosure relates to lightening the appearance of skin tissue using cooling or cryogenic techniques, and in particular a cosmetic method and apparatus that can facilitate such lightening.

BACKGROUND

Hyperpigmentation of skin may lead to darkened areas such as freckles, age spots, 'café au lait' spots, or 'bags' under the eyes. Hyperpigmentation can result from a variety of factors such as UV exposure, aging, stress, etc. These factors can lead to an excess production of melanin, or melanogenesis, in the skin by melanocytes, which can lead to formation of hyperpigmented areas.

There may be a demand for cosmetic products that can lighten the appearance of skin, either for overall lightening of the complexion or for lightening particular hyperpigmented regions thereof such as large freckles, 'café au lait' spots, or 'bags' under the eyes that may result from excessive local amounts of pigment in the skin. Many topical formulations are being marketed that claim to lighten age spots and reduce the effects of hyperpigmentation. However, these cosmetic formulations may have questionable effectiveness.

Hypopigmentation of skin tissue has been observed in response to temporary cooling or freezing of the tissue, such as may occur during cryosurgery procedures. Such hypopigmentation effects that can be generated by contact cooling are described, e.g., in Y. Har-Shai et al., "Effect of Skin Temperature on Skin Pigmentation During Contact and Intralesional Cryosurgery of Keloids," JEADV 2007, 21, 191-198 (2006). Loss of pigmentation following skin cooling or freezing may result from decreased melanosomes production, destruction of melanocytes, or inhibited transfer of melanosome into the keratinocytes in the lower region of the epidermal layer. The resultant hypopigmentation may be long-lasting or permanent.

Accordingly, there may be a need for methods and apparatus that can provide controlled and/or gradual lightening of skin tissue that can address and/or overcome at least some of the deficiencies or issues described herein above.

SUMMARY

Exemplary embodiments of the present disclosure relate to apparatus and method for reducing overall pigmentation of an area of skin using cryogenic techniques. In one exemplary embodiment of the present disclosure, an apparatus can be provided for cooling or freezing small regions of skin to produce a lightening of the skin appearance.

According to an exemplary embodiment of the present disclosure, the apparatus can include a plurality of protrusions, e.g., protrusions or tapered points, having a large thermal capacity. For example, the protrusions can be made at least partially of a metal or alloy, such as brass, gold, copper, or the like, diamond or diamondlike carbon, a frozen material, or another material that can preferably exhibit a high heat capacity, such as diamond. One or more of the protrusions can also be formed using a frozen material that can preferably exhibit a high heat capacity. The protrusions can be attached to a base, which can also be formed at least partially of a material having a high heat capacity. An insulated handle or cover can be provided for the base. The exemplary apparatus can be placed in a freezer such that the protrusions are cooled to subzero temperatures, and then positioned such that the tips of the protrusions contact an area of skin to be treated.

In further exemplary embodiments of the present disclosure, the base of the apparatus can be at least partially hollowed out to form a reservoir. A refrigerant or other heat-absorbing medium, such as saline solution or water-alcohol solution, can be provided in the reservoir to cool the base and attached protrusions. Optionally, a cooled refrigerant can be circulated through the reservoir and/or one or more ducts formed in the reservoir to provide continuous cooling to the base and attached protrusions.

In another exemplary embodiment of the present disclosure, a Peltier device or other cooling arrangement can be provided in thermal contact with the base and/or the protrusions to cool the plurality of protrusions.

In still further exemplary embodiments of the present disclosure, the distal portion of the protrusions can be formed using a material having a high thermal conductivity, such as diamond, gold, copper, or the like. The total area of the distal portions of the protrusions configured to contact the skin tissue can be less than proximal portions of the high-conductivity material that are in thermal communication with the base or other thermal mass. For example, the total area of the distal ends can be less than about 0.4 times the area of the proximal portion of the high-conductivity material, or less than about 0.2 times this area. This ratio of areas facilitates small portions of skin contacting the distal ends of the protrusions to be in an efficient thermal communication with a larger area of the base or other thermal mass that is provided at a lower temperature, which can provide more rapid and effective local cooling of the skin portions.

In yet another exemplary embodiment of the present disclosure, the protrusions can be configured to penetrate the skin surface, for example, to approximately the depth of the dermal-epidermal junction, which can be about 0.1 mm (100 μm). These protrusions can have a sharp tip and a narrow conical or pyramidal shape. For example, the distance between the lower surface of the base and the tip of each protrusion can be between about 50 μm and about 500 μm, or about 100 μm. An insulating layer can be provided on a lower surface of the base between these sharp protrusions to inhibit cooling of the skin surface between the sharp protrusions when they are inserted into the upper portion of the skin.

In a further exemplary embodiment of the present disclosure, an apparatus can be provided that include a plurality of thermally conductive arrangements that are in thermal communication with a base. For example, an insulating layer can be provided between the thermally conductive arrangements such that the distal ends of the thermally conductive arrangements are substantially coplanar with a lower surface of the insulating layer. This exemplary apparatus can provide an extraction of heat from spatially separated regions of skin tissue through the thermally conductive arrangements and into the base while inhibiting or preventing significant heat extraction from areas of tissue between these spatially separated regions.

In still another exemplary embodiment of the present disclosure, an apparatus can be provided that includes an insulating layer provided on a lower surface of a base that has a high thermal conductivity and/or a high specific heat capacity. The insulating layer can be provided with a plurality of small openings, e.g., having a width of less than about 1 mm. Spatially separated regions of skin can be placed in direct contact with portions of the lower surface of the base through these small openings to provide extraction of heat therefrom, whereas the insulating layer can inhibit or prevent significant heat extraction from areas of tissue between these openings in the insulating layer.

In a further exemplary embodiment of the present disclosure, a cosmetic method can be provided to produce hypopigmentation in skin tissue. In one exemplary embodiment, the method for lightening the appearance of skin can be provided that includes cooling an/or freezing a plurality of small skin regions to induce localized hypopigmentation effects. The individual areas that are cooled or frozen can have a maximum dimension along the skin surface of less than about 1 mm, or less than about 0.8 mm, or less than about 0.5 mm. Smaller areas can also be cooled or frozen. For example, the distance between the cooled or frozen regions can be greater than about 3 times a diameter or width of the regions, or greater than about 5 times this diameter or width of the regions. Such small and separated frozen regions area can provide a more gradual overall lightening, and prevent a visual appearance of discrete depigmented regions. Further lightening can be achieved by treating a particular region of skin more than once.

In a still further exemplary embodiment of the present disclosure, the cosmetic method can include cooling and/or freezing small separated regions of skin tissue using a plurality of small cold objects such as, e.g., tip portions of an array of cold protrusions or a plurality of thermally conductive protrusions, to reduce and/or eliminate expression of pigmentation in the cooled or frozen regions. The width or diameter of the frozen regions can be less than about 1 mm, less than about 0.8 mm, less than about 0.5 mm, or about 0.1 mm. The average separation distance between these cooled or frozen regions can be, e.g., greater than about 3 times the width or diameter of the regions, or greater than about 5 times this width or diameter. The regions of skin can be frozen, for example, to at least the depth of the dermal-epidermal junction to provide a hypopigmentation effect. Hydroquinone or cortisone can be applied topically to the surface regions of skin tissue after they have been frozen to inhibit any possible hyperpigmentation in or around these regions.

This exemplary method can provide gradual lightening of the area being treated by forming very small depigmented areas without forming individual depigmented spots that may be apparent to the naked eye. Multiple treatments can be used to lighten the area further. The exemplary methods and apparatus described herein may also produce a rejuvenating effect on the skin tissue and/or improve the general appearance thereof by stimulating a healing effect in the small regions of tissue damaged by the cooling or freezing.

These and other objects, features and advantages of the present disclosure will become apparent upon reading the following detailed description of embodiments of the invention, when taken in conjunction with the appended claims.

BRIEF DESCRIPTION OF DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

According to an exemplary embodiment of the present disclosure, a "fractional cryotherapy" approach can be used to gradually reduce overall darkness of skin areas resulting from excess pigmentation. Small regions of skin can be contacted with cold objects to inhibit formation and/or expression of pigment in the underlying skin. This effect can provide permanent and gradual lightening of the areas being treated.

Figure 1:
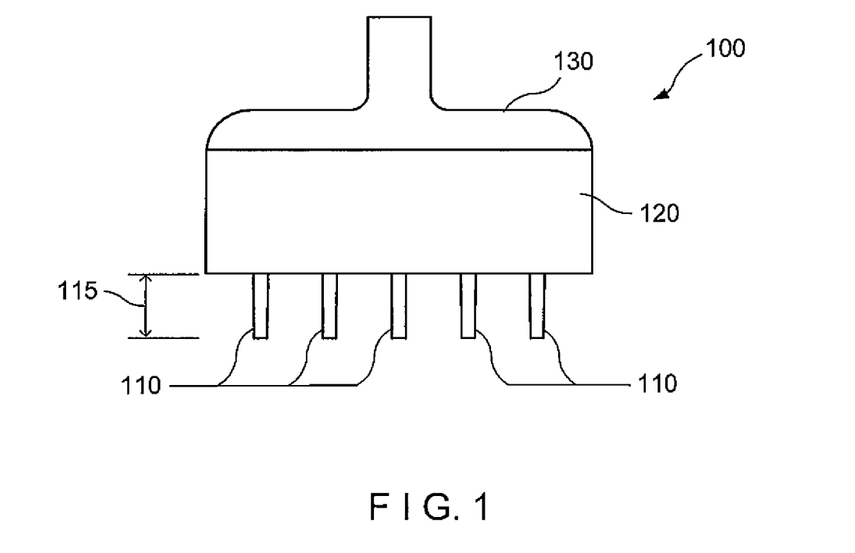
FIG. 1 is a side view of a first exemplary apparatus that can be used to produce a hypopigmentation cryogenically in a skin tissue.

FIG. 1 depicts an exemplary apparatus 100 for producing controlled amounts of hypopigmentation in skin tissue in accordance with exemplary embodiments of the present disclosure. The exemplary apparatus 100 can include a plurality of protrusions 110 attached to a base 120. The protrusions 110 can be provided in a thermal communication with the base 120. In certain exemplary embodiments, the protrusions 110 and the base 120 can be formed from a single material. An insulating handle 130 can be affixed to the base 120 to facilitate handling and positioning of the apparatus 100. Further, the general dimensions of the base 120 are not limited to the proportions illustrated in the FIG. 1. For example, the base 120 can be provided as a plate or substrate that is relatively thin from top to bottom as compared to the lateral dimensions.

The protrusions 110 can be formed from a metal or a metal alloy, or another material having a high specific heat capacity and/or a high thermal conductivity, e.g., values of these thermophysical properties that are greater than the corresponding values for the skin tissue. For example, the protrusions 110 can be made of brass, copper, silver, aluminum, graphite, diamond, diamondlike carbon, other materials which are used in conventional contact cryoprobes, or combinations thereof. The base 120 can be formed from the same material or another material having similar thermal properties. For example, materials having a much higher thermal conductivity than the skin tissue can be used to facilitate an extraction of heat from the portion of the tissue contacted by the cooled protrusions 110. Further, materials having a much higher specific heat capacity than the skin tissue can be held at a cold temperature, and extract heat from the portion of tissue contacted by the cooled protrusions 110. The distal ends of the protrusions 110 can be substantially flat and/or slightly rounded to provide good thermal contact with skin tissue when the apparatus 100 is placed on the area of the skin to be treated.

In one exemplary embodiment, the protrusions 110 can be formed of a metal such as copper, silver, or brass. A layer or coating of diamond, diamondlike carbon, or another material having a higher thermal conductivity can optionally be provided on the distal ends of the protrusions 110. Diamond has a very high thermal conductivity, and a layer of diamond on the distal ends of the protrusions 100 can improve thermal contact between the cooled protrusions 110 and the skin being treated.

The exemplary apparatus 100 can be placed in a freezer to cool the protrusions 110 and the base 120. Alternatively, the protrusions 110 and/or the base 120 can be cooled by spraying them with a refrigerant such as liquid nitrogen, or immersing them in a cold bath, such a chilled solution of alcohol and water or a cold saline solution. Preferably, the bath can be maintained at a predetermined temperature. After cooling, the distal ends of the protrusions 110 can then be pressed against an area of skin to be lightened for a predetermined time, which can locally chill and/or freeze a plurality of spots within the area.

Figure 2:
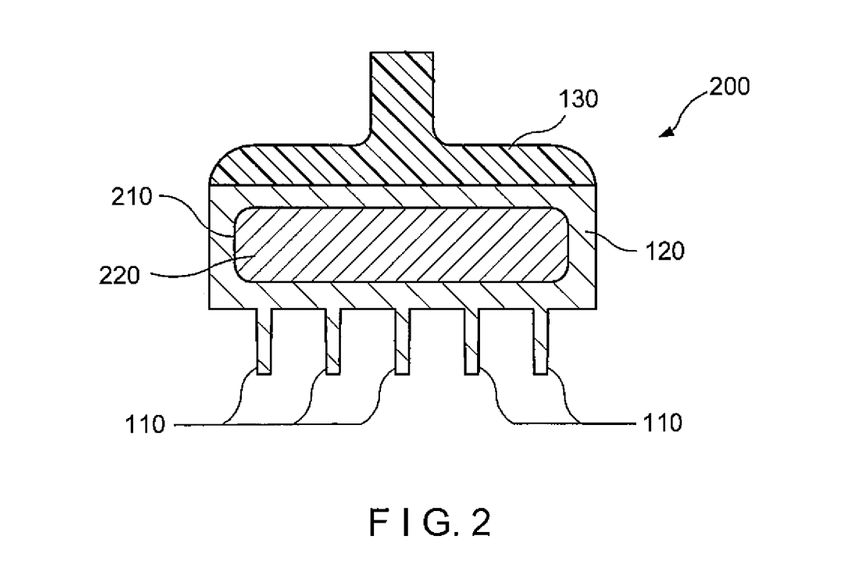
FIG. 2 is a side cross-sectional view of a second exemplary apparatus that can be used to produce the hypopigmentation cryogenically in the skin tissue.

In a further exemplary embodiment shown in FIG. 2, an apparatus 200 can be provided that is similar to the exemplary apparatus 100 shown in FIG. 1. The base 120 of the apparatus 200 can include a hollow reservoir 210 which contains a refrigerant 220. The refrigerant 220 can be a material that freezes, for example, at a temperature below 0 degrees Celsius. Such a refrigerant 220, when frozen in the reservoir 210, can facilitate cooling of the base 120 and/or the protrusions 110 at colder temperatures for a longer period of time.

In certain exemplary embodiments of the present disclosure, the refrigerant 220 can be selected such that it exhibits a solid-liquid phase change at a particular temperature or a temperature range. For example, when the exemplary apparatus 200 warms up to the phase change temperature (if it is initially colder), the refrigerant 220 can facilitate a maintenance of the base 120 and/or the protrusions 110 at approximately the phase change temperature or within a particular phase change temperature range for an extended period of time (e.g., during longer contact periods between the protrusions 110 and the skin tissue being treated, or during application of the apparatus 200 to a plurality of regions of skin being treated). Heat extracted from the skin tissue can be conducted through the protrusions 110 and the base 120 to the refrigerant 220, which can absorb the heat at a relatively constant temperature as the phase change in the refrigerant 220 progresses. This exemplary arrangement can facilitate a predictable and repeatable rate of heat transfer flow from the skin contacting the protrusions 100 because the temperature difference provided by the apparatus 200 can be maintained substantially constant.

A thermal conduction between the distal ends of the protrusions 110 and the base 120 can be reduced if the protrusions 110 have a large aspect ratio (e.g., the length 115 is significantly larger than the diameter or width of the protrusions 110). With such a large aspect ratio, the distal ends of the protrusions 110 may tend to warm up when contacting the skin tissue, even though the base 120 is at a colder temperature. The protrusion lengths 115 can be long enough to prevent the base 120 from directly contacting the skin surface, but short enough to provide a good thermal communication between the distal ends of the protrusions 110 and the base 120.

For example, the length 115 of the protrusions 110 extending from the lower surface of the base 120 can be less than about 1 cm, or less than about 5 mm. Such a short protrusion length 115 can facilitate heat flow between the distal ends of the protrusions 110 which are placed in contact with the skin tissue being treated and the base 120, by providing a shorter path for heat flow. Accordingly, heat can be extracted more rapidly from the regions of the skin contacting the distal ends of the protrusions 110, facilitating faster and more efficient local freezing of the tissue. The protrusions 110 can be long enough such that the lower surface of the base 120 does not contact the surface of the skin when the distal ends of the protrusions 110 are placed against the skin surface.

The protrusions 110 can be provided with an approximately circular cross-sectional shape. The cross-sectional shape can refer to the shape of a section that is substantially parallel to the lower surface of the base 120 and/or substantially parallel to the skin surface when the protrusions 110 are contacting the skin surface. Other cross-sectional shapes may be used, such as square, rectangular, hexagonal, ovoid, and the like. Further, the cross-sectional shape of the distal or tip portion of the protrusions 110 can have a different cross-sectional shape than other portions of the protrusions 110. For example, the distal end of a protrusion 110 can be provided with a substantially circular cross-sectional shape, whereas a proximal portion of the protrusion 110 can be square or rectangular in cross section. The distal portion of the protrusions 110 can have cross-sectional shapes, for example, that are round, square, polygonal, ovoid, or irregular. Other shapes can also be used. The cross-sectional shape of this distal portion of the protrusions 110 can approximately correspond to, for example, the shape of the portion of skin tissue that directly contacts the protrusion 110. Resiliency of the skin tissue can alter the shape of this contact area when the distal ends of the protrusions 110 are placed against the skin surface.

The diameter or width of the distal end of each protrusion 110 can be less than about 1 mm, less than about 0.8 mm, or less than about 0.5 mm. In certain exemplary embodiments of the present disclosure, this diameter can be about 0.1 mm. Smaller diameters can be more suitable for treating darker skin to avoid formation of easily visible high-contrast depigmented spots. Alternatively, larger diameters or widths can be used to treat lighter skin or darker pigmented regions of lighter skin. These sizes are generally smaller than those associated with conventional cryoprobes. The small distal ends can facilitate formation of distinct small regions of skin tissue that can be cooled or frozen, and thereby depigmented, without being individually visible to the naked eye.

Figure 3A:
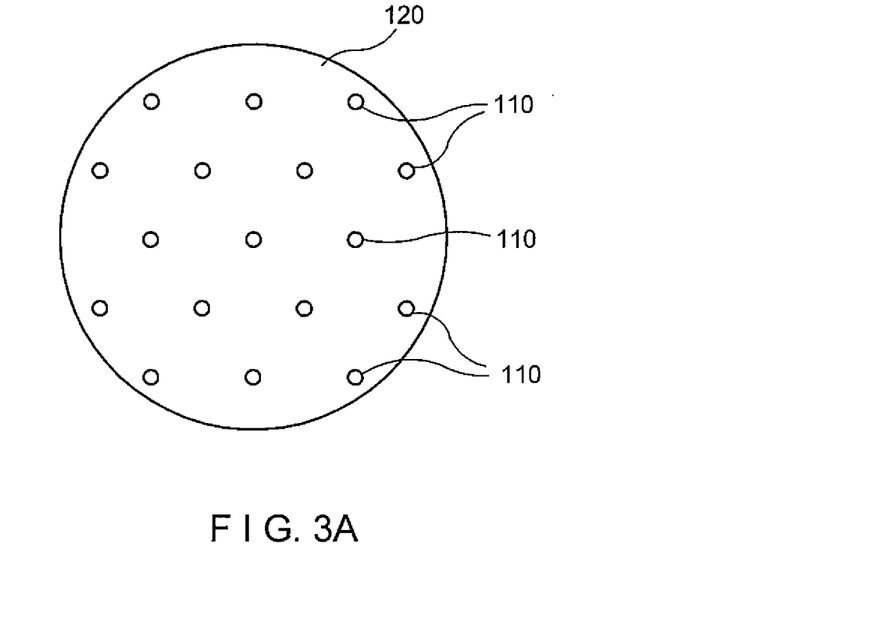
FIG. 3A is a bottom view of a first exemplary configuration of protrusions that can be used to produce the hypopigmentation in the skin tissue.

An exemplary array of distal ends of the protrusions 110 protruding from the base 120 is shown in FIG. 3A. The protrusions 110 can be provided in a regular hexagonal arrangement, which can form a corresponding uniform spacing of frozen regions of skin tissue when the chilled protrusions 110 are placed against the skin. Other regular exemplary arrangements can also be used, such as square or rectangular arrays, etc.

The distance between distal ends of the adjacent protrusions 110 can be relatively large as compared to their diameter or width. For example, the average distance between the distal ends of the adjacent protrusions 110 can be, e.g., greater than about 3 times an average diameter or width of the distal ends, or greater than about 5 times this average diameter. Larger distances between the distal ends of the adjacent protrusions 110 can also be used, e.g., distances greater than about 10 times the diameter. These exemplary configurations, distal end sizes, and separation distances between the distal ends can facilitate a formation of small spatially separated depigmented portions of the tissue that have unaffected tissue between them. This can provide a gradual lightening of the area of the tissue being treated without generating individual depigmented spots that may be visible to the naked eye. The distances between the distal ends that are smaller than about 3 times the average width of the distal ends can also be provided in certain exemplary embodiments, where more extensive local depigmentation can be desired.

Figure 3B:
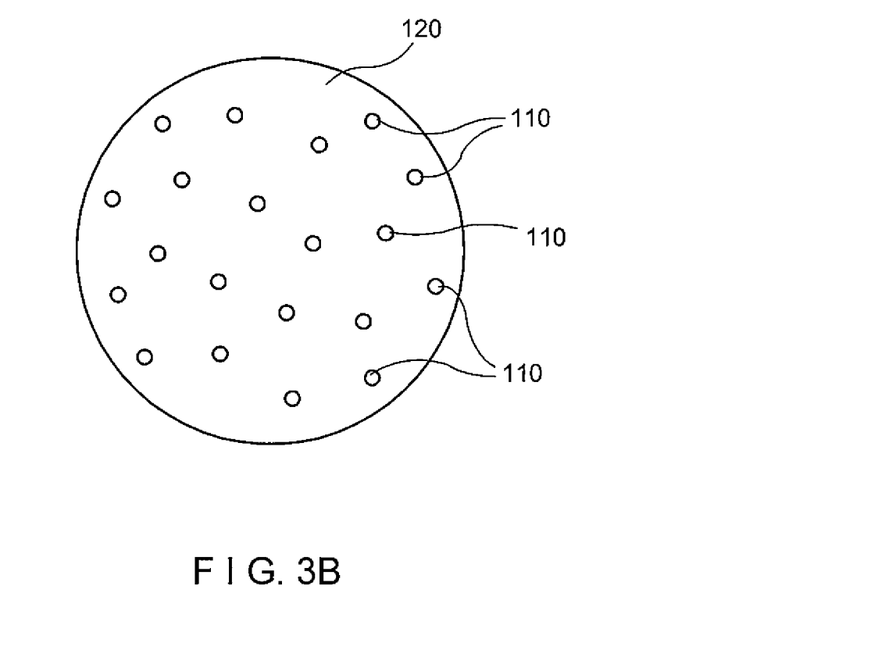
FIG. 3B is a bottom view of a second exemplary configuration of the protrusions that can be used to produce the hypopigmentation in the skin tissue.

An irregular (e.g., random or semi-random) arrangement of the protrusions 110 can also be used, as shown in FIG. 3B. Such an irregular array can provide reduced clustering of the treated regions and an appearance of more uniform depigmentation if the exemplary apparatus 100 shown in FIG. 1 or the exemplary apparatus 200 shown in FIG. 2 can be applied a plurality of times to a single area of the skin in different orientations. The average distances between the distal ends of the protrusions 110 shown in FIG. 3B can be similar to the distances described herein for the protrusions 110 shown in FIG. 3A, although the distances between adjacent protrusions 110 illustrated in FIG. 3B may not be uniform.

The exemplary sizes, spacings, and configurations of the distal ends of the protrusions 110 described herein can provide cooling or freezing, and subsequent depigmentation, of small regions of skin that are not easily visible to the naked eye while maintaining pigmented areas between the frozen regions to produce a slight overall lightening of the skin appearance.

The cross-sectional shape of the base 120 shown in FIGS. 3A and 3B is substantially circular. Other shapes may also be used in accordance with further embodiments of the present disclosure. For example, the cross-sectional shape of the base 120 can be elliptical or oval, square, rectangular, or irregular. The particular shape of the base 120 can be selected based on the area being treated. For example, an elongated crescent-shaped base 120 can be used to lighten bags under the eyes.

The size of the base 120 can also be selected based on the size of the area being treated. For example, depigmentation of small areas can be achieved using a relatively small base 120 having few protrusions 110. Larger bases 120 having more protrusions 110 can be provided to treat larger areas of the skin with a single application. The protrusion sizes and spacings can be provided as described herein for various sizes of the base 120.

In general, the number and configuration of the protrusions 110 may be selected to provide appropriate patterns of depigmented spots for particular treatments. For example, devices having just the few closely-spaced protrusions 110 (e.g., less than about 10 or 15 protrusions 110 where, e.g., the spacing between the distal ends thereof are about, e.g., 3 times the diameter of these distal ends) can be used for lightening small age spots. Larger numbers of the protrusions 110 can be provided on the larger base 120 to lighten larger areas of skin with a single treatment.

The exemplary apparatus 100 or the exemplary apparatus 200 can be cooled, for example, by placing the entire apparatus in a freezer and/or by exposing it to another cold material or environment. The protrusions 110 can be cooled to a temperature at which they can induce contact freezing in skin tissue. The base 120 can also cooled to the same temperature. The cooled base 120 can provide a thermal sink that can help maintain the protrusions 110 at or close to the cooled temperature while portions of the apparatus 100 (e.g., distal ends of the protrusions 110) are in contact with skin tissue.

Figure 4A:
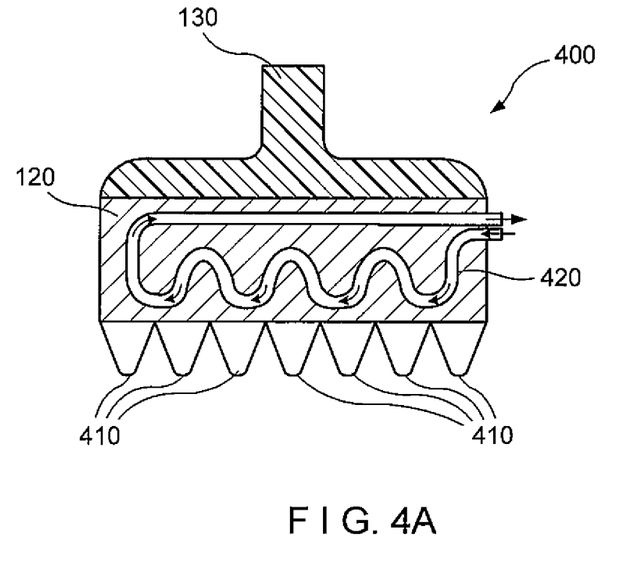
FIG. 4A is a side cross-sectional view of a third exemplary apparatus that can be used to produce the hypopigmentation cryogenically in the skin tissue.

In a further exemplary embodiment of the present disclosure, an exemplary apparatus 400 can be provided as shown in FIG. 4A. The base 120 of the exemplary apparatus 400 can include one or more channels 420 therethrough. A cooled refrigerant can be circulated through the channels to cool the base 120 and the protrusions 410, and optionally to maintain them at a particular temperature. For example, a conventional fluid pump (not shown) can be used to circulate a cooling medium through the channels 420 in the base 120. Such pump can be located remotely from the apparatus 400, or it can be affixed to the apparatus 400. The refrigerant can also be provided in a reservoir (not shown) that can be insulated or actively cooled using conventional techniques. The reservoir can also be located remotely from the apparatus 400 or affixed thereto.

The protrusions 410 can be tapered as shown in FIG. 4, and can be formed using a material with large thermal conductivity as described herein. For example, the protrusions 410 can have a conical or pyramidal shape, or the like. The diameter or width of the proximal ends of the protrusions 410 can be, e.g., at least 2 times the width or diameter of the distal ends thereof. Such tapered shapes can provide good thermal communication between the distal ends of the protrusions 410 and the cooled base 120. For example, the tapered protrusions 410 can facilitate an extraction of heat from a small region of the tissue contacting the distal end of the protrusions 410 through a larger area of the base 120 that is in thermal communication with the proximal end of the protrusions 410.

Figure 4B:
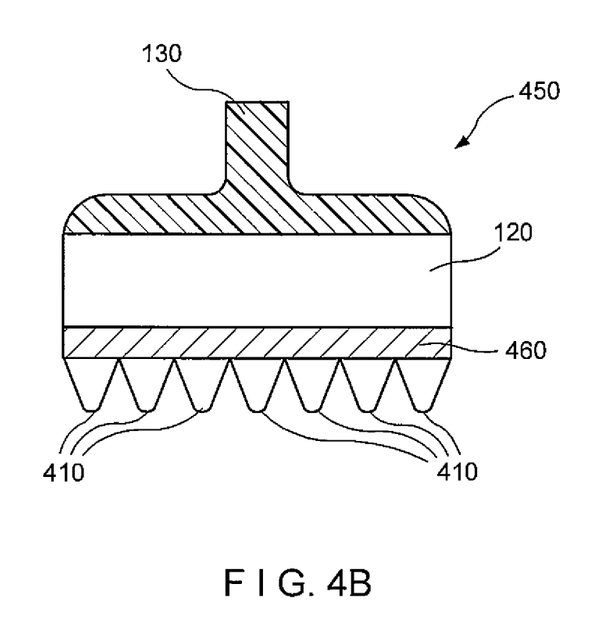
FIG. 4B is a side cross-sectional view of a fourth exemplary apparatus that can be used to produce the hypopigmentation cryogenically in the skin tissue.

In yet another exemplary embodiment of the present disclosure, an exemplary apparatus 450 can be provided as shown in FIG. 4B. A layer 460 of material having a high thermal conductivity can be affixed to a lower surface of the base 120 and provided in a good thermal contact therewith. The layer 460 can be provided, for example, as a plate, or as a film deposited on the lower surface of the base 120. The protrusions 410 can be tapered as described herein, and provided in thermal contact with the layer 460. Alternatively, the layer 460 and the protrusions 410 can be formed as a single component from a high conductivity material, e.g., brass, diamond, or the like. Similar to the exemplary apparatus 400 shown in FIG. 4, the tapered protrusions 410 can facilitate the extraction of heat from a small region of tissue contacting the distal end of the protrusions 410 that are in thermal communication with a larger area of the base 120 through the protrusions 410 and the plate 460.

Figure 5:
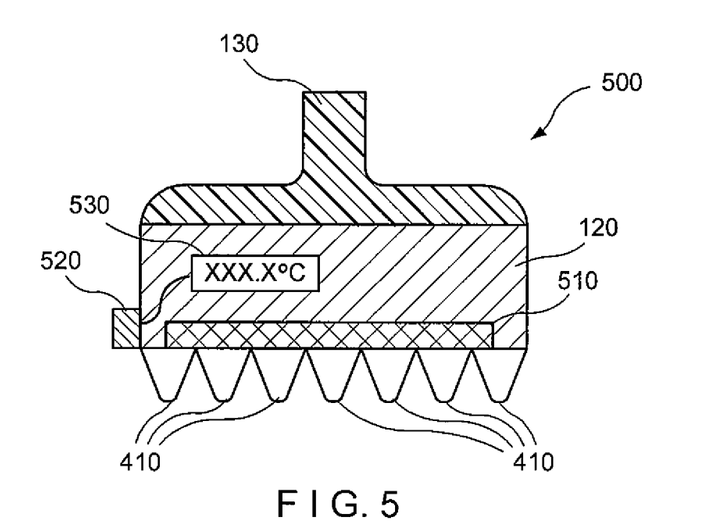
FIG. 5 is a side cross-sectional view of a fifth exemplary apparatus that can be used to produce the hypopigmentation cryogenically in the skin tissue.

In a still further embodiment of the present disclosure, an exemplary apparatus 500 can be provided as shown in FIG. 5. The base 120 can include one or more Peltier devices 510. The cold side of the Peltier device 510 can be provided in thermal contact with the protrusions 410 and/or the lower portion of the base 120. A power source for powering the Peltier device 510 can be provided as part of the apparatus 500, or alternatively the power source can be separate therefrom. The upper portion of the Peltier device 510 can be cooled by contacting it with a cooled object, by allowing air to flow over at least a portion of it, and/or by other conventional techniques.

A temperature sensor 520 can be provided proximal to the lower portion of the base 120 or the protrusions 410. The temperature sensor can include, e.g., one or more thermocouples or thermistors or the like. Such temperature sensor 510 can be connected to a display 520 to indicate the temperature of the apparatus 500 near the protrusions 410. The temperature sensor 520 can also be connected to the Peltier device 510 or any other active cooling arrangement as part of a control system to maintain the base 120 and/or protrusions 410 at or near a predetermined temperature.

Figure 6:
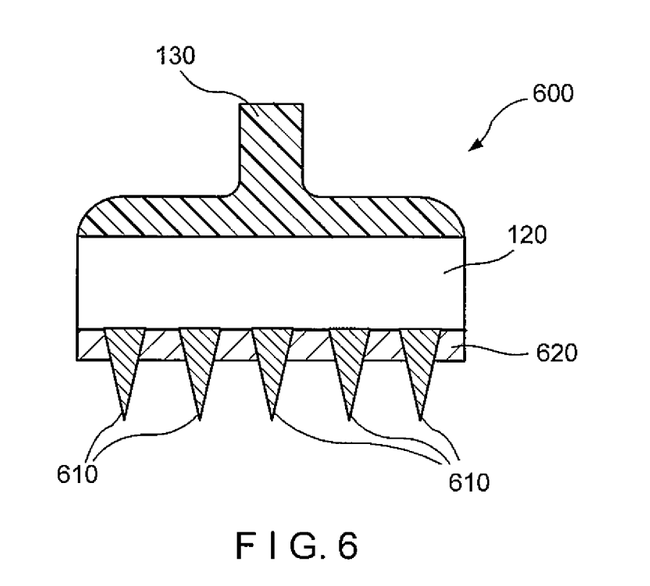
FIG. 6 is a side cross-sectional view of a sixth exemplary apparatus that can be used to produce the hypopigmentation cryogenically in the skin tissue.

In yet another exemplary embodiment, an exemplary apparatus 600 shown in FIG. 6 can be provided that include a plurality of thermally conductive protrusions 610 that are in thermal communication with a lower portion of the base 120. The protrusions 610 can be configured to pierce the surface of the skin, e.g., to approximately the depth of the dermal/epidermal junction or slightly deeper. For example, the protrusions 610 can be provided with a sharp distal end and a narrow profile to facilitate piercing of the skin tissue. This exemplary configuration can provide a more effective cooling or freezing of tissue just below the skin surface while being only minimally invasive. A thermally insulating layer 620 can be provided on the lower surface of the base 120 between the protrusions 610 projecting therefrom.

The lower portion of the apparatus 600 can be pressed onto the area of skin to be treated. The protrusions 610 can pierce the skin, and extract heat to cool or freeze small regions of adjacent tissue. The portions of the skin surface between the protrusions 610 can contact the insulating layer 620, which can both control the penetration depth of the protrusions 610 and inhibit cooling of these portions by the cooled base 120.

The protrusions 610 can be formed from material having a high thermal conductivity, such as diamond or diamond-like carbon, certain metals, etc. The length of the protrusions 610 can be selected to approximately match the depth of the dermal/epidermal junction in the area of skin being treated. For example, the distance between the lower surface of the insulating layer 620 and the distal end, or tip, of each protrusion 610 can be between about 50 μm and about 500 μm, or more preferably about 100 μm. This distance can be selected based on the local depth of the dermal/epidermal junction. This distance can also be varied by altering the thickness of the insulating layer 620, which can be removable or detachable from the base 120.

The protrusions 610 can be provided with a conical or pyramidal shape that includes a sharp tip for piercing the skin surface and a wider proximal end in contact with the base 120 for an improved thermal communication. Pyramidal shapes having 3, 4, 6, or any other number of sides may be used. The ratio of the length of each protrusion 610 to the width of the proximal end can be at least about 2:1, or preferably at least about 3:1. Such aspect ratios, which correspond to relatively narrow protrusions 610, can facilitate penetration of the protrusions 610 into the epidermis.

Various combinations of the protrusion shapes and features, cooling arrangements, and other apparatus features described herein can also be used in exemplary embodiments of the present disclosure, where certain combinations may not be explicitly illustrated or described.

The temperature of the cooled protrusions 110, 410, 610 can be less than about −4 degrees Celsius to provide hypopigmentation effects in the cooled or frozen skin. Colder temperatures can be used, for example, the temperatures that can be as low as −20 or −30 degrees Celsius. The temperature can preferably be low enough to locally freeze at least a portion of the epidermal layer of the skin tissue proximal to the distal ends of the cooled protrusions 110, 410, 610 when these distal ends are brought into contact with the area of the skin to be treated.

The distal ends of the protrusions 110, 410, 610 can be placed in contact with the region of the skin being treated for a duration of time sufficient to generate subsequent hypopigmentation of the frozen regions. Portions of the upper dermal layer can also be frozen. This time duration can be greater than about 15 seconds. However, the time of contact should not be so long as to cause excessive freezing and issue damage in the cooled or frozen tissue. The time of contact should also not be so long as to induce substantial freezing and subsequent hypopigmentation in the portions of skin tissue between the distal ends of the protrusions 110, 410, 610. Accordingly, the time of contact can be selected or controlled without an excessive or any undue experimentation to provide portions of skin tissue between the regions of skin contacted by the cooled protrusions that do not undergo a significant degree of hypopigmentation based on the cooling or freezing of nearby tissue. In general, an appropriate time of contact can be determined based on the geometry, materials, and initial cooled temperature of the exemplary embodiments of the apparatus described herein.

The particular contact duration used to achieve good hypopigmentation results can be determined for a particular apparatus being used, a particular subject's skin characteristics, and the apparatus temperature. For example, a few trial tests can be performed with a particular apparatus at a constant initial cooled temperature for several contact times, to determine a preferred or optimal contact time for a particular patient based on observed pigmentation responses. Alternatively, a few different initial temperatures can be tested with a particular apparatus and contact time. In general, the time and temperature used can be selected to produce a small zone of frozen tissue around each of the protrusions 110, 410, 610, while maintaining unfrozen skin in a significant portion of the skin tissue therebetween.

In certain exemplary embodiments, the material and size (e.g., diameter, shape and length 115) of the protrusions 110, 410, 610 can be selected such that the corresponding apparatus is initially cooled, and the protrusions 110, 410, 610 gradually warm up during prolonged contact with skin tissue. Accordingly, the protrusions 110, 410, 610 can be provided in contact with the skin for longer periods of time, and gradual warming of the protrusions 110, 410, 610 can prevent excessive freezing of the regions of skin proximal thereto.

Figure 7A:
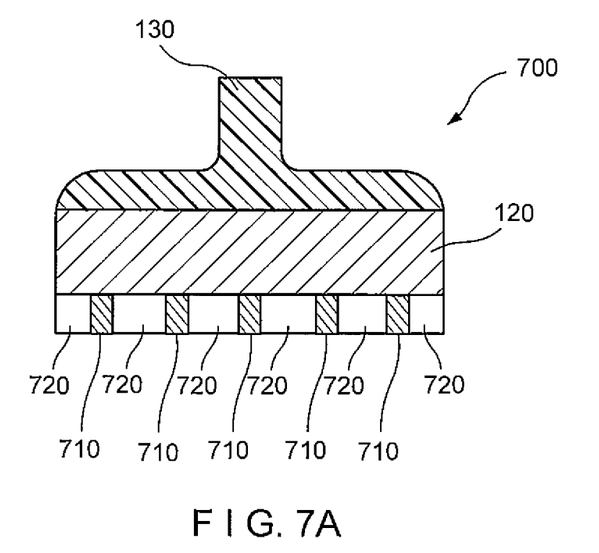
FIG. 7A is a side cross-sectional view of a seventh exemplary apparatus that can be used to produce the hypopigmentation cryogenically in the skin tissue.

FIG. 7A illustrates a further exemplary apparatus 700 for producing controlled amounts of hypopigmentation in skin tissue in accordance with exemplary embodiments of the present disclosure. The exemplary apparatus 700 can include, e.g., a plurality of thermally conductive arrangements 710 that can extend through a discontinuous insulating layer 720 attached to a base 120. The conductive arrangements 710 can be formed, at least in part, using the materials having a high thermal conductive and/or high specific heat capacity as described herein for the protrusions 110. The conductive arrangements 710 can be provided in a thermal communication with the base 120. In certain exemplary embodiments, the conductive arrangements 710 and at least one portion (or a plurality of portions) of the base 120 can be formed from a single material. The base 120 can be cooled using any of the procedures or arrangements in the various exemplary embodiments described herein. An insulating handle 130 can be affixed to the base 120 to facilitate handling and positioning of the exemplary apparatus 700.

A lower surface of the exemplary apparatus 700 can be substantially flat, or it can have a curved or contoured shape configured to correspond to a particular area of skin to be treated. This lower surface may be placed against an area of skin to be treated. The distal ends of the conductive arrangements 710 can then contact spatially separated regions of the skin tissue to cause local cooling and/or freezing of these regions, as described in detail herein. The insulating layer 720 can provide a thermal barrier that facilitates a prevention of heat extraction from the skin tissue between the distal ends of the conductive arrangements 710.

The size, shape, arrangement and/or spacings of the distal ends of the conductive arrangements 710 can include any of the corresponding parameters for distal ends of the protrusions 110 described in detail herein. For example, a width of a cross-section of at least one distal end of at least one of the thermally conductive arrangements can be less than about 1 mm. The thickness of the insulating layer 720 (and length of the conductive arrangements 710) can be large enough to provide sufficient thermal isolation of the skin surface between the conductive arrangements 710 to prevent substantial cooling or freezing thereof. This thickness can be selected based on the material(s) used to form the insulating layer 720, which can include any appropriate materials having a relatively low thermal conductivity. The thickness of the insulating layer 720 and length of the conductive arrangements 710 can also be small enough to facilitate an efficient extraction of heat from the regions of skin tissue through the conductive arrangements 710.

Figure 7B:
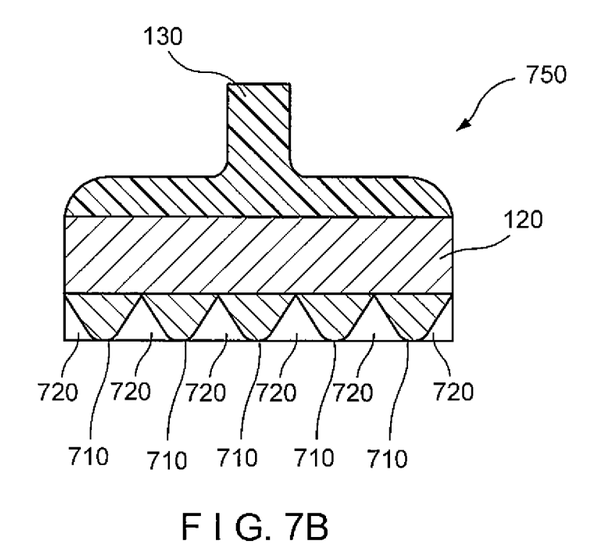
FIG. 7B is a side cross-sectional view of an eighth exemplary apparatus that can be used to produce the hypopigmentation cryogenically in the skin tissue.

FIG. 7B depicts a further exemplary apparatus 750 in accordance with exemplary embodiments of the present disclosure, that is similar to the exemplary apparatus 700 shown in FIG. 7A. For example, the thermally conductive arrangements 710 in the exemplary apparatus 750 can be provided with a tapered shape, such that the areas of the proximal ends of the conductive arrangements 710 that are in direct thermal contact with the base 120 are larger than the areas of the distal ends that may be placed in direct contact with the surface of the skin tissue. Such a tapered geometry can facilitate more efficient conduction of heat away from the spatially separated regions of skin tissue through the conductive arrangements 710 and into the cooled base 120. This effect of a tapered shape on heat conduction is described in more detail herein with respect to the tapered protrusions 410 shown in FIGS. 4A and 4B. A discontinuous insulating layer 720 can be provided between the tapered conductive arrangements 710 to reduce an amount of heat extraction from the skin tissue between the distal ends of the conductive arrangements 710, as described above with respect to the exemplary apparatus 700.

Figure 8:
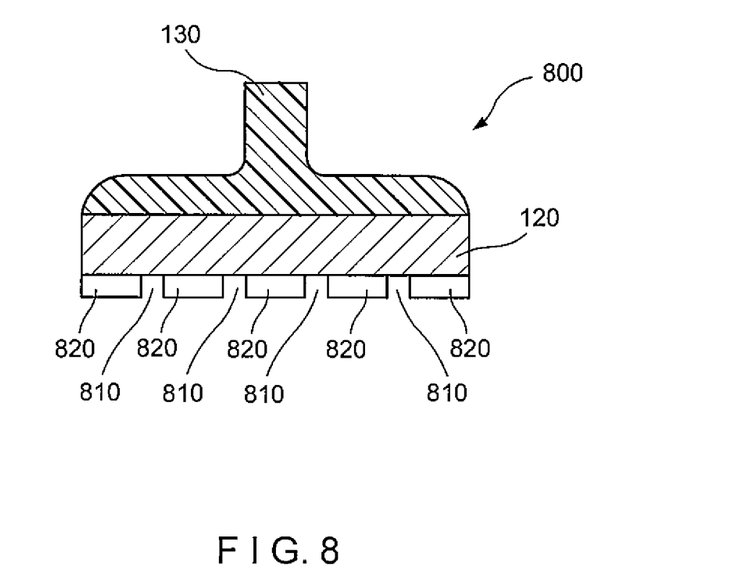
FIG. 8 is a side cross-sectional view of a ninth exemplary apparatus that can be used to produce the hypopigmentation cryogenically in the skin tissue.

FIG. 8 depicts a still further exemplary apparatus 800 for producing controlled amounts of hypopigmentation in skin tissue in accordance with exemplary embodiments of the present disclosure. The exemplary apparatus 800 can include a discontinuous insulating layer 820 affixed to a lower surface of a base 120. The base 120 can be cooled using any of the procedures or arrangements in the various exemplary embodiments described herein. An insulating handle 130 can be affixed to the base 120 to facilitate handling and positioning of the apparatus 800.

A lower surface of the exemplary apparatus 800 can be substantially flat, or it may have a curved or contoured shape configured to correspond to a particular area of skin to be treated. This lower surface can be placed against an area of skin to be treated. A plurality of openings 810 provided in the discontinuous insulating layer 820 can allow spatially separated regions of the skin to directly contact a lower surface of the base 120 through these openings 810. These spatially separated regions of the skin tissue can then be cooled and/or frozen, as described in detail herein, to produce small regions of hypopigmentation. The insulating layer 820 can provide a thermal barrier that facilitates a prevention of heat extraction from the skin tissue between the plurality of openings 810. For example, a width of at least one of the openings can be less than about 1 mm The size, shape, arrangement and/or spacings of the openings 810 can include any of the corresponding parameters for distal ends of the protrusions 110 described in detail herein. The thickness of the insulating layer 820 can be large enough to provide sufficient thermal isolation of the skin surface between the openings 810 to prevent substantial cooling or freezing thereof, and small enough to facilitate direct contact between the lower surface of the base 120 and regions of the skin surface when the apparatus 800 is placed against the skin.

Multiple fractional cryotherapy treatments in accordance with any of the exemplary embodiments described herein can be performed on a particular area of the skin to produce further lightening of the skin. The multiple treatments can preferably be performed at longer intervals, e.g., days or weeks, to allow hypopigmentation effects from a particular treatment to become visually evident before subsequent treatments are performed. Such exemplary multiple treatments can be used to gradually lighten the skin appearance in the treated area. Because the depigmented spots are spatially separated, multiple treatments may be applied to a single area without producing discernible white spots.

In further exemplary embodiments of the present disclosure, a method can be provided for gradually and controllably lightening the appearance of skin tissue by generating hypopigmentation using cryogenic techniques. A plurality of spatially-separated small regions of the epidermal skin tissue can be cooled or frozen to induce hypopigmentation. The size of the spatially-separated frozen regions can be less than about 1 mm, or more preferably less than about 0.5 mm. Portions of the upper dermal layer beneath the frozen epidermal regions can also be frozen or cooled during such exemplary procedures.

The distance between adjacent frozen regions of skin can be greater than about 3 times the diameter or lateral dimension of the frozen regions along the tissue surface, or greater than about 5 times this diameter. These exemplary distance ratios can facilitate a preservation of unaffected and normally pigmented portions of skin between the frozen regions. Accordingly, the exemplary cryogenic hypopigmentation method(s) described herein can provide a gradual lightening of the area of skin being treated without producing readily discernible depigmented spots. Freezing of the skin tissue can be achieved by contact cooling, e.g., using an exemplary apparatus as described herein. Alternatively, such depigmentation can be produced by spraying a cryospray or applying a cold substance through a mask that protects certain regions of the skin surface being treated while allowing the cryospray to contact and freeze spatially-separated regions of the skin surface.

In certain exemplary embodiments, a substance such as hydroquinone or cortisone may be applied topically to the treated areas after the small regions of skin have been frozen. Such a substance can reduce formation of undesirable hyperpigmentation around the peripheral portions of the frozen regions and/or reduce inflammation caused by the freezing process.

The exemplary procedures described herein can be repeated on a particular area of skin to further lighten it. Preferably, the interval between successive procedures can be long enough to allow the hypopigmentation effects to be visibly evident and to better control the overall degree of lightening obtained. Multiple procedures can also be repeated at shorter intervals if desired, for example, to provide a greater overall degree of hypopigmentation in a first area of skin as compared to a second area, using a particular apparatus having a particular size and spacing of protrusions to provide contact cooling.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents and publications cited herein are incorporated herein by reference in their entireties.

What is claimed is:

1. A method for producing controlled amounts of hypopigmentation in a skin tissue of a patient, the method comprising:
   identifying an area of the skin tissue to be treated with hypopigmentation;
   contacting without penetrating the area of the skin tissue to be treated with a skin treatment device, the skin treatment device having a contact end comprising a plurality of cooling rods each having a distal end configured for a non-penetrating contact with a surface of the skin tissue area to provide heat extraction from the area of the skin tissue; and
   locally freezing the area of the skin tissue proximal to the distal ends of the plurality of cooling rods to generate subsequent hypopigmentation in the area of the skin tissue, the contact end of the skin treatment device being in thermal communication with a cooling arrangement, the cooling arrangement configured to cool each of the plurality of cooling rods to a temperature between −4° C. to −30° C.; and freezing a dermal-epidermal junction of the area of the skin tissue;
   wherein each of the plurality of cooling rods have a width of greater than 0.1 mm and a spacing between each of the plurality of cooling rods greater than 5 mm so as to effect fractional cryotherapy of the skin tissue.

2. The method of claim 1, wherein the distal ends of the plurality of cooling rods are contacted with the area of the skin tissue to be treated for a predetermined amount of time, wherein the distal ends of the plurality of cooling rods are configured to transfer heat from the distal ends of the plurality of cooling rods to the cooling arrangement only by conduction.

3. The method of claim 2, wherein the cooling arrangement comprises a thermoelectric cooler.

4. The method of claim 3, further comprising maintaining the thermoelectric cooler at a predetermined temperature using a control arrangement.

5. The method of claim 4, wherein the control arrangement includes a temperature monitor comprising at least one thermistor or thermocouple.

6. The method of claim 1, wherein insulation is provided between the plurality of cooling rods.

7. The method of claim 1, wherein the local freezing of the area of the skin tissue area decreases melanosome production or melanosome transfer to keratinocytes.

8. The method of claim 1, wherein the local freezing of the area of the skin tissue area destroys melanocytes.

9. The method of claim 1, wherein a cross-sectional shape of each of the plurality of cooling rods is selected from the group consisting of circular, elliptical, oval, square, and rectangular.

10. The method of claim 1, wherein the spacing between each of the plurality of cooling rods is selected to effect hypopigmentation in spatially separated regions of the area of the skin tissue area with unaffected tissue between the spatially separated regions.

11. The method of claim 1, wherein the area of the skin tissue area is contacted with the contact end of the skin treatment device for greater than 15 seconds.

12. The method of claim 1, wherein the contact end of the skin treatment device is contacted with the area of the skin tissue area for a predetermined amount of time which locally freeze the area of the skin tissue that is contacted by the contact end.

13. The method of claim 1, further comprising repeating the contacting and locally freezing steps on a previously identified and treated skin tissue area to further lighten the skin tissue.

14. The method of claim 1, wherein the area of the skin tissue area comprises one or more freckles, and wherein the hypopigmentation lightens the one or more freckles.

15. The method of claim 1, wherein the area of the skin tissue area comprises one or more age spots, and wherein the hypopigmentation lightens the one or more age spots.

16. The method of claim 1, wherein the area of the skin tissue area comprises one or more café au lait spots, and wherein the hypopigmentation lightens the one or more café au lait spots.

17. The method of claim 1, further comprising applying a substance topically to the skin tissue area after freezing the dermal-epidermal junction of the area of the skin tissue; to reduce inflammation.

18. A method for producing controlled amounts of hypopigmentation in skin tissue of a patient, the method comprising:
   identifying an area of skin tissue to be treated with hypopigmentation;
   contacting without penetrating the area of skin tissue to be treated with a skin treatment device, the skin treatment device having a contact end comprising a plurality of cooling rods each having a distal end configured for a non-penetrating contact with a surface of the area of the skin tissue area to provide heat extraction from the area of the skin tissue area; and locally freezing separated surface regions of the area of the skin tissue area proximal to the distal ends of the plurality of cooling rods to generate subsequent hypopigmentation in the separated surface regions of the area of the skin tissue; the separated surface regions of the area of the skin tissue; being separated by unfrozen tissue regions, the contact end of the skin treatment device being in thermal communication with a cooling arrangement, the cooling arrangement configured to cool each of the plurality of cooling rods to a temperature between −4° C. to −30° C.; and freezing a dermal-epidermal junction of the area of the skin tissue; and wherein a width of each of the separated surface regions of the area of the skin tissue is greater than 0.1 mm and a spacing between each of the separated surface regions of the area of the skin tissue is greater than 5 mm so as to effect fractional cryotherapy of the skin tissue.

* * * * *